United States Patent
Peng et al.

(10) Patent No.: US 9,867,851 B2
(45) Date of Patent: Jan. 16, 2018

(54) FOOD FOR NUTRITIONAL THERAPY OF AIDS

(71) Applicants: Du Peng, Jiangyin (CN); Jianjiang Si, Jiangyin (CN)

(72) Inventors: Du Peng, Jiangyin (CN); Jianjiang Si, Jiangyin (CN)

( * ) Notice: Subject to any disclaimer, the term of this patent is extended or adjusted under 35 U.S.C. 154(b) by 607 days.

(21) Appl. No.: 14/396,963

(22) PCT Filed: Apr. 26, 2013

(86) PCT No.: PCT/CN2013/074756
§ 371 (c)(1),
(2) Date: Oct. 24, 2014

(87) PCT Pub. No.: WO2013/159730
PCT Pub. Date: Oct. 31, 2013

(65) Prior Publication Data
US 2015/0118220 A1  Apr. 30, 2015

(30) Foreign Application Priority Data
Apr. 26, 2012 (CN) .......................... 2012 1 0126929

(51) Int. Cl.
| | | |
|---|---|---|
| *A61K 36/07* | (2006.01) | |
| *A61K 35/00* | (2006.01) | |
| *A61K 36/062* | (2006.01) | |
| *A61K 36/53* | (2006.01) | |
| *C12P 1/00* | (2006.01) | |
| *A23L 31/00* | (2016.01) | |
| *A23L 33/105* | (2016.01) | |

(52) U.S. Cl.
CPC .............. *A61K 35/00* (2013.01); *A23L 31/00* (2016.08); *A23L 33/105* (2016.08); *A61K 36/062* (2013.01); *A61K 36/07* (2013.01); *A61K 36/53* (2013.01); *C12P 1/00* (2013.01); *A61K 2236/00* (2013.01)

(58) Field of Classification Search
None
See application file for complete search history.

(56) References Cited

FOREIGN PATENT DOCUMENTS

| | | |
|---|---|---|
| CN | 1098244 A | 2/1995 |
| CN | 1363371 A | 8/2002 |
| CN | 1416741 A | 5/2003 |
| CN | 1995323 A | 7/2007 |
| CN | 101099845 A | 1/2008 |
| CN | 102133283 A | 7/2011 |
| WO | 2013/159730 A1 | 10/2013 |

*Primary Examiner* — Qiuwen Mi
(74) *Attorney, Agent, or Firm* — Maschoff Brennan

(57) ABSTRACT

The present invention relates to food for nutritional therapy of AIDS belonging to functional foods. It is made from deep fermentation of *Morchella* spp and *Tricholoma matsutake* in traditional Chinese medicine medium extracting from *Callicarpa bodinieri*. The combination and synergistic effect of the food components could alleviate fear of chill caused by large number of broken erythrocyte in patients with AIDS, improve immunity effectively, ameliorate symptoms and physical signs, promote body activities, further postpone complication occurrence and improve patient's quality of life.

13 Claims, No Drawings

FOOD FOR NUTRITIONAL THERAPY OF AIDS

TECHNICAL FIELD

The present invention relates to functional foods, particularly to a food for nutritional therapy of Acquired Immune Deficiency Syndrome (AIDS).

BACKGROUND

Acquired Immune Deficiency Syndrome (AIDS) is a syndrome that occurs when a human is infected by Human Immunodeficiency Virus (HIV) to result in immunodeficiency and simultaneous eruption of a series of opportunistic infections and tumors, in severe cases, death will be caused. Currently, the mortality rate of AIDS is as high as 100%, and AIDS has been classified as category B infectious disease and one of infectious diseases monitored by international health and quarantine organizations. AIDS is called as "super fatal disease" and has become public health problem which severely threaten human health in the world.

Caecotrophy will further injure physiological function on the basis of the injury on immune system, which reduces AIDS patients' life quality, daily activity, shortens survival time and affects therapy effects of AIDS medicines. Because large numbers of erythrocytes are destroyed, AIDS patients are fearful of common colds and other ordinary illnesses. Due to deteriorating bodily function, absorbance to nutrient substance of AIDS patients becomes worse, which will result in the aggravation of erythrocyte damage, a vicious cycle that accelerates the disease course. Thus, ensuring the supply and absorbance of nutrients is the most important demand of AIDS patients.

Nutrition support therapy is to prevent and correct caecotrophy which has arisen or may arise during the disease course and therapy of patients. Nutrition support therapy includes enteral nutrition therapy and parenteral nutrition therapy. Enteral nutrition (EN) is providing nutrient substance required by organism metabolism through mouth and feeding tube. Parenteral nutrition (PN) is providing complete and sufficient nutrients through intravenous route in order to meet vital requirements. All nutrient substances are offered to fasting patients through intravenous route, which is called as total parenteral nutrition (TPN).

SUMMARY

AIDS nutrition support therapy according to embodiments of the invention satisfies nutrient needs of AIDS patients, improves nutritional status of patients, enhances tolerance to therapy, promotes recovery and prevention of AIDS, cures caecotrophy, strengthens organism defense capacity, reduces complications, control opportunistic infections, lowers mortality rate, makes AIDS patients accept therapy smoothly, slows development of disease course, increases AIDS patients' life quality and extends their life cycle.

With the decrease of immunity in patients with AIDS, complications are common, and the survival quality of the patients in final stage is very low. Although there is no effective cure so far, health protection means that can enhance life quality, slow disease progression speed, which is good news for AIDS patients.

In view of the demand and blank of above-mentioned field, this invention aims to provide a food (also referred to as "nutritional supplement") for nutritional therapy of AIDS.

Said food is made of Chinese traditional medicine materials or food materials. It can alleviate symptom of fear of common colds and other ordinary illnesses due to a great deal of damage of erythrocyte, and enhance immunity effectively without toxicity.

A food for nutritional therapy of AIDS, is prepared by deep fermentation of maternal strains hypha of common morel (*Morchella* spp) and maternal strains hypha of *matsutake* mushroom (*Tricholoma matsutake*) in traditional Chinese medicine liquid medium, and said traditional Chinese medicine liquid medium is water-leach liquor of crude drug of purple pearl (*Callicarpa bodinieri*)

The weight ratio between the original crude drug and the final water-leach liquor of the crude drug is 4~5%.

Said traditional Chinese medicine liquid medium also comprises an adjuvant, the components of said adjuvant (part by weight) are as follows: 1 part of pulse flour, 1 part of corn flour, 2 parts of white sugar, 0.1 parts of dipotassium hydrogen phosphate, 0.1 part of potassium dihydrogen phosphate, 0.05 parts of magnesium sulfate.

Said water-leach liquor is extracted from root of purple pearl (*Callicarpa bodinieri*).

The form of the food is granules, soup or powder. The application of the food, wherein the application refers to the food as a component is added into food prepared for AIDS patients.

According to an embodiment, the preparation method of said food, comprise steps as follows:

(1) preparing a water-leach liquor of the crude drug purple pearl (*Callicarpa bodinieri*)
(2) Diluting the water-leach liquor by adding 20~25 times of water in volume to obtain the traditional Chinese medicine liquid medium;
(3) Injecting maternal strains of common morel (*Morchella* spp) and *matsutake* mushroom (*Tricholoma matsutake*) in said traditional Chinese medicine liquid medium and conducting deep fermentation.

In step (1), the weight ratio between the original crude drug and the final water-leach liquor of the crude drug is 4~5%. In step (2), adding the adjuvants into the water-leach liquor, wherein the added adjuvants has 4~5 times of weight of the crude drug; then conducting elixation; the constituents of said adjuvants (part by weight) are as follows: 1 part of pulse flour, 1 part of corn flour, 2 parts of white sugar, 0.1 parts of dipotassium hydrogen phosphate, 0.1 parts of potassium dihydrogen phosphate, 0.05 parts of magnesium sulfate.

Said deep fermentation comprises: inactivating by water vapour under ordinary pressure, cooling to 26±2° C.; fermenting for 60~144 hours. Said water-leach liquor is extracted from root of purple pearl (*Callicarpa bodinieri*).

In said food for nutritional therapy of this invention, nutrients in purple pearl (*Callicarpa bodinieri*) and edible fungi coordinate to strengthen physical function of the whole body and each organ of AIDS patients, as well as relieve the symptom of fear of chill by protecting erythrocyte and enhancing regenerative capacity of erythrocyte of AIDS patients. Clinical tests prove, the food can be effective to improve survival quality, increase body weight, strengthen immunity, and recover activity and relieves pain.

Root, stem, leaf, flower and/or seed of purple pearl (*Callicarpa bodinieri*) can be used as medicine. According to records in medicine prior arts, the purple pearl (*Callicarpa bodinieri*) has pharmaceutical effects of clearing heat, detoxication, blood-cooling, stanch bleeding, reducing inflammation, promoting tissue regeneration, anti-tumor and etc. Different parts of purple pearl (*Callicarpa bodinieri*) can cure different diseases with significant effects. The water-leach liquor of the root of purple pearl (*Callicarpa bodinieri*) is used to cure ocular infection, fever, thirst, dysentery, relieving itching; the leaf is used for curing spitting blood, hemoptysis, hematochezia, uterine bleeding, traumatic hemorrhage. The leaf and young stem of purple pearl (*Callicarpa bodinieri*) can be collected in spring, summer, autumn, and used directly or dried in the sun and grinded. The root can be collected in four seasons, sliced and dried in the sun.

Said edible fungi of this invention comprise common morel (*Morchella* spp) and *matsutake* mushroom (*Tricholoma matsutake*). Maternal strains of common morel (*Morchella* spp) and that of *matsutake* mushroom (*Tricholoma matsutake*) are mixed and fermented with water-leach liquor of purple pearl (*Callicarpa bodinieri*). By means of stains fermentation, combining alimentotherapy effects of the two edible fungi and pharmaceutical effects of the purple pearl (*Callicarpa bodinieri*) to relieve the symptom of fear of chill and a series of complications due to erythrocyte damage of AIDs patients.

*Matsutake* mushroom (*Tricholoma matsutake*) (Accc51588) is a famous and precious edible fungi, and deemed as "the king of edible fungi". As with rich nutrients, delicious taste and fragrance, *matsutake* mushroom become a precious dish on banquet. *Matsutake* mushroom (*Tricholoma matsutake*) has 17% crude proteins, 5.8% crude fat, 61.5% soluble non-nitrogen compound as well as rich vitamins B1, B2, C, nicotinic acid calcium, phosphorus, iron and etc. It can strengthen health, benefit intestines and stomach, relieve pain, regulate qi-flowing for eliminating phlegm, expel parasite and etc, and it is effective to restrain glycuresis and inhibit tumor. It is recorded in some Japanese references that, effective rate of anti-tumor of *matsutake* mushroom (*Tricholoma matsutake*) has reached 90%. *Matsutake* mushroom (*Tricholoma matsutake*) also has high economy value. Its sale price in international market is about 30~50 thousands dollars per ton, which is higher than other fungi.

Common morel (*Morchella* spp): Accc51837, is also called as *morchella*, which is hypha of *Morchella angusticeps* Peck (Pezizales, Morohellaceae, *Morchella*). It is widely distributed in Henan, Shanxi, Gansu, Qinghai, Xizang, Xinjiang, Sichuan, Shanxi, Jilin, Jiangsu, Yunnan, Hebei, Beijing and etc in China. It is first recorded in "Xinhua materia medica outline" that: effects of Common morel (*Morchella* spp) are harmonizing stomach, helping digestion, regulating qi-flowing for eliminating phlegm. It's mainly effective for food stagnation, abdominal fullness and distention, phlegm, circulation of vital energy in the wrong direction and dyspnea with cough. It is sweet and mild and mainly effective on spleen and stomach.

Common morel (*Morchella* spp) contains polysaccharide for inhibiting tumor as well as active ingredients for anti-bacteria and anti-virus and can strengthen organism immunity. High level of selenium contained by *Morchella* spp, which is essential consisitituent of glutathione peroxidase in human erythrocyte, can transport numerous oxygen to inhibit cancer by inactivating cancer cells and strengthen anti-oxidization of vitamin E. According to records in "The Chinese Materia Medica" that: the Common morel (*Morchella* spp) it is sweet, cold and non-toxic; it's beneficial to intestine and stomach, and it reduces phlegm, regulates the flow of vital energy and remove obstruction to it; it's mainly effective for indigestion, excessive phlegm and cough. its feature is sweet and mild; it's beneficial to intestine and stomach, digestion, reducing phlegm, regulating the flow of vital energy and remove obstruction to it, tonifying kidney-yink, nourishing brain and refreshing; it has good effects on weakness of the spleen and the stomach, indigestion, excessive phlegm, breathe hard, dizziness insomnia.

Common morel (*Morchella* spp) has high level of organic germanium, which strengthens health, prevents cold and enhances organism immunity. And it has various essential mineral substances the contents of kalium and phosphorus in every 100 gram of dry *Morchella* spp are 7 times and 4 times respectively of that in Chinese caterpillar fungus; the content of zinc in every 100 gram of dry *Morchella* spp is 4.3 times of that in shii-take mushroom, 4 times of that in *hericium erinaceus*; the content of iron in every 100 gram of dry *Morchella* spp is 31 times of that in shii-take mushroom, 12 times of that in *hericium erinaceus*" (cited from "Chinese medicinal mycology", published in 1997). In this invention, the common morel (*Morchella* spp) can be substituted by *morchella conica* Fr., *Morchella conica* Pers, *Morchella crassipes* (Vent.) Pers., since these *Morchella* spp are almost the same to the common morel (*Morchella* spp) in the present invention on flavor, nature and effect.

So far, there is not any report about effects of said two edible fungi on treating AIDS. In this invention, the effects of benefiting stomach and intestine, regulating the flow of vital energy and remove obstruction to it, enhancing kidney function, as well as anti-virus of said two fungi are exploited, and the effects of removing the necrotic tissue and promoting granulation as well as anti-inflammatory of *Callicarpa bodinieri* are combined by co-fermentation. It is assumed that interaction and combination occur during fermentation, which brings the food the effects of relieving the symptom of fear of chill of AIDS patients, alleviating a series of complications due to erythrocyte damage, slowing disease course and improving survival quality of AIDS patients.

During preparation, 60~140 hours of fermentation can ensure complete fermentation high level of effective solid substances and polysaccharide, and ideal therapy effect. the fermentation time also depends on temperature outside fermenter, nutrients and oxygen content of medium during fermentation.

Said food of this invention takes co-fermentation products of *Callicarpa bodinieri*, *Morchella* spp and *Tricholoma matsutake* as effective ingredients. During preparation, water-leach liquor of *Callicarpa bodinieri* is used as fermentation medium for the *Morchella* spp and *Tricholoma matsutake*. In one embodiment, adjuvants for fermentation are added in the water-leach liquor of *Callicarpa bodinieri*. It is indicated by clinical data that adjuvants added in a proper proportion does not affect the efficacy of said food of this invention.

The *Morchella* spp and *Tricholoma matsutake* are mixed and injected into the water-leach liquor of *Callicarpa bodinieri*, in which the deep fermentation is conducted. Fermentation liquor obtained is filtered, and the filter residue was dried and prepared into granules with 0.34 g. The granules are proper for oral administration with dosage of no less than 6 pills and no more than 18 pills. Taking the food continually 10 days will let the AIDS patients get better life quality efficiently. The filtrate was sterilized and prepared as soup or conducted concentration and crystallization to be prepared as powder. The soup or powder can be added to daily food as nutritional food for AIDS patients. Taking 2.04~6.12 g the soup or the powder or food that containing 2.04~6.12 g of the soup or the powder every day can effectively strengthen immunity of AIDS patients, prevent complications, relieve symptoms and enhance organism activity.

As step of the preparation process includes conducting deep fermentation by adding maternal strains of *Morchella* spp and *Tricholoma matsutake* into water-leach liquor of *Callicarpa bodinieri* flower, stem, leaf or seed and obtaining fermentation liquor. The filter residue of the fermentation liquor is dried and prepared as granules; the filtrate was sterilized and then prepared as soup or conducted concentration and crystallization to be prepared as powder. Said granules, soup or powder is taking by AIDS patients directly or added into their daily food as nutritional food. Taking the food continually can effectively strengthen immunity of AIDS patients, prevent complications, relieve symptoms and improve organism activity.

Said nutritional food of this invention is organic combination of various constituents, and plays effects relying on coordination between various active ingredients. It can regulate organism status, effectively prevent erythrocyte decay, relieve and cure the symptom of fear of chill of AIDS patients, further improve health by means of nutritional supplement, increase immunity, accordingly to inhibit complications and sufficiently exert effect of each ingredient in the food.

The nutritional food of this invention has been taken by 160 AIDS patients, their symptom of fear of chill is relieved gradually or even disappears, and other accompanied symptoms of fear of chill are also relieved gradually. And no other new complication raised basically. Combining with the therapy of other AIDS medicine, their life quality is significantly improved, and the total effective rate is above 96%.

Said granules, soup or powder can be used as food additive to make food for preventing AIDS. Eating food adding said granules, soup or powder in long term can effectively prevent the symptom of fear of chill of AIDS patients.

Preparation of said food in this invention is simple and fit for scaled production for corporation. Said food has little side effects, lasting therapy effect, and it's affordable for AIDS patients; it can prevent and relieve the symptom of fear of chill, enhance organism immunity, improve physical signs, strengthen organism activity and increase life quality of AIDS patients.

BRIEF DESCRIPTION OF SELECTED EMBODIMENTS

Materials:

Root of purple pearl (*Callicarpa bodinieri*) was removed its bark, and adopted its meat quality; 1 kg the meat quality was added 20~25 Kg water and boiled for 50 minutes to obtain 20~25 kg water-leach liquor No. 1 of purple pearl (*Callicarpa bodinieri*).

Maternal strains of *Morchella* spp and Maternal strains of *Tricholoma matsutake* were obtained by spore separation method. Their hyphae cultured on slant or plate were selected by microscopy and stored at 4° C. with storage period less than 90 days.

Maternal strains of *Morchella* spp and *Tricholoma matsutake* adopted in this invention were tube maternal strains (tube specification is 18 mm of diameter×180 mm of height) and purchased from Agricultural Culture Collection of China, the Chinese Academy of Agricultural Sciences. The *Tricholoma matsutake* has the deposit No.: Accc51588; the *Morchella* spp has the deposit No.: Accc51837.

Said maternal strains are also stored at the applicant's laboratory, and can be delivered to public for research use in 20 years from the application filing date.

Embodiment 1. Preparation of Food No. 1

The water-leach liquor No. 1 of purple pearl (*Callicarpa bodinieri*) was added 20~25 times volume of drinking water to gain a traditional Chinese medicine liquid medium. Said traditional Chinese medicine liquid medium was poured into 200 L fermenter, which is recorded in utility model patent "tank cover of culture tank for liquor strain of edible fungi and culture tank" with the patent No. CN03270560.3. There must be 15% space left in fermenter and injected moderate antifoaming agents or defoamer (said antifoaming agents or defoamer is conventional agents for edible fungi fermentation, and its selection as well as the selection on its consumption is conventional); with flange cover locked, said fermenter was pushed into "the saturated steam pressureless boiler" (patent no. 200320126611.8) for inactivation for 12 hours. When the fermenter was cooled to 26° C., the purchased tube maternal strains of *Morchella* spp and *Tricholoma matsutake* were respectively injected into said fermenter (patent No. 03270560.3), and every 50 L traditional Chinese medicine liquid medium were injected with one tube maternal strains of *Morchella* spp and one tube maternal strains of *Tricholoma matsutake* by injector recorded in "injection rod for edible fungi liquor and injector containing said injection rod" (patent no. 200320126960.X). After 60~144 hours of fermentation, fermenter was opened, and the obtained fermentation liquor was filtered. The filter residue was dried to prepare granules; the filtrate was inactivated and divided into two sections for preparing soup and powder respectively.

Granules gained by the above-mentioned process is proper for oral administration for AIDS patients with dosage of no less than 6 pills and no more than 18 pills. Taking the granules once every day for continuous 10 days will be effective to relieve or even cure the symptom of fear of chill.

Said soup or powder or other food forms that prepared with said soup or powder by conventional process, e.g. nutrition powder, congee or gruel, are suitable for AIDS patients. Eating the food containing 2.04~6.12 g the soup or the powder every day for continuous 10 days will relieve or even cure the symptom of fear of chill, and relieve other symptoms of complications correspondingly, and improve life quality obviously.

Said granules, soup or powder can be used as food addictive to prepare food for AIDS patients. Eating the food added with said granules, soup or powder in long term can effectively prevent the symptom of fear of chill of AIDS patients.

Maternal strains of *Morchella* spp and *Tricholoma matsutake* used in this invention are purchased from Agricultural Culture Collection of China, Soil and Fertilizer Institute of the Chinese Academy of Agricultural Sciences. They are also stored at the applicant's laboratory, and can be delivered to public for research in 20 years from the application filing date.

Embodiment 2. Preparation of Food No. 2

The water-leach liquor No. 1 of *Callicarpa bodinieri* was added 20~25 times volume of drinking water and other adjuvants (1 portion of pulse flour, 1 portion of corn flour, 2 portion of white sugar, 0.1 portion of dipotassium hydrogen phosphate, 0.1 portion of potassium dihydrogen phosphate, 0.05 portion of magnesium sulfate), which has 4~5 times of weight of *Callicarpa bodinieri* and is used to increase the density of fermentation, to gain a traditional Chinese medicine liquid medium. Said traditional Chinese medicine liquid medium was poured into 200 L fermenter, which is recorded in utility model patent "tank cover of culture tank for liquor strain of edible fungi and culture tank" with the patent No. CN03270560.3. There must be 15% space left in fermenter and injected moderate antifoaming agents or defoamer (said antifoaming agents or defoamer is conventional agents for edible fungi fermentation, and its selection as well as the selection on its consumption is conventional); with flange cover locked, said fermenter was pushed into "the saturated steam pressureless boiler" (patent no. 200320126611.8) for inactivation for 12 hours. When the fermenter was cooled to 26° C., the purchased tube maternal strains of *Morchella* spp and *Tricholoma matsutake* were respectively injected into said fermenter (patent No. 03270560.3), and every 50 L traditional Chinese medicine liquid medium were injected with one tube maternal strains of *Morchella* spp and one tube maternal strains of *Tricholoma matsutake* by injector recorded in "injection rod for edible fungi liquor and injector containing said injection rod" (patent no. 200320126960.X). After 60~144 hours of fermentation, the fermenter was opened and the obtained fermentation liquor was filtered. The filter residue was dried to prepare granules; the filtrate was inactivated and divided into two sections for preparing soup and powder respectively.

Granules gained by the above-mentioned process is proper for oral administration for AIDS patients with dosage of no less than 6 pills and no more than 18 pills and taking the granules continually 10 days will be effective to relieve or even cure the symptom of fear of chill. Eating food containing 2.04~6.12 g of said soup or powder once every day for continuous 10 days can relieve the symptom gradually and enhance life quality obviously.

Said granules, soup or powder can be used as food addictive to prepare food for AIDS patients. Eating food added with said granules, soup or powder in long term can effectively improve immunity.

Maternal strains of *Morchella* spp and *Tricholoma matsutake* used in this invention are purchased from Agricultural Culture Collection of China, Soil and Fertilizer Institute of the Chinese Academy of Agricultural Sciences. They are also stored at the applicant's laboratory, and can be delivered to public for research in 20 years from the application filing date.

Example 1. Application Effect of Granules of Food Obtained in Embodiment. 1

In this invention, standard of life quality refers to the quality of life questionnaire for Chinese cancer patients (QLQ-CCC) compiled by Professor Yan SUN of department of internal medicine, the Affiliated Tumor Hospital of China Academy of Medical Science, which is for assessing life quality of AIDS patients. There are 12 items including mental state, appetite, sleeping, symptom, therapy, understanding & support, daily life, and etc., set forth in QLQ-CCC; in each item, there are 5 grades from 1 to 5 points; high score means better life quality; full score is 60 points, and lowest score is 12 points; if the score is lower than 20 points, life quality is very bad; if 21-30 points, life quality is bad; 31-40 points means ordinary in life quality; 41-50 points means well, 51-60 points means better. AIDS patients fill in QLQ-CCC once before and after eating said food in this invention.

There were 100 volunteers with AIDS, whose blood examination result was HIV positive (+). Before this test, all of them have one or more of the following symptoms: fever, shiver with cold, joint pain, muscle pain, vomit, diarrhea, laryngalgia with persistent fever, night sweat, enervation, systemic superficial lymphadenopathy, body weight loss over 10% in 3 months even 40% at most, becoming thin obviously, appetite decreasing, apocleisis, sicchasia, hematochezia, dizziness, headache, lags in response, hypophrenia, insanity, convulsions, hemiplegic paralysis, dementia, diffuse papules, acute posterior ganglionitis, inflammation and fester in oral cavity and pharyngeal mucosa. Taking said granules of food No. 1 once every day for continuous 10 days, it's indicated in 96 volunteers that their symptoms of pains and fear of chill were relieved and even disappeared; other complications were relieved obviously and even disappeared. And there was no new complication raised in any one, and their mental states became better. Furthermore, according to the data distribution of life quality score before and after taking granules of food no. 1, the total effective rate reaches 96%. The data distribution of life quality score before and after eating granules of food no. 1 is shown in table 1.

Table 1 the data distribution of life quality score before and after eating said granules of food obtained in embodiment 1

| Number of AIDS patients | Time | life quality score (point) | | | | |
| --- | --- | --- | --- | --- | --- | --- |
| | | <20 | 21-30 | 31-40 | 41-50 | 51-60 |
| 100 | Before eating granules of food no. 1 | 4 | 44 | 40 | 10 | 2 |
| | After eating granules of food no. 1 | 0 | 4 | 36 | 48 | 12 |

Typical Case:

Name: XXX; sex: X; born in XX; address: XX; profession:

Blood examination result: HIV positive (+)

Symptoms: apocleisis, fatigue and lack of strength, diarrhoea, dizziness, headache, lags in response, hypophrenia, insanity, systemic pruritus. XXX took granules of food No. 1. During the period of taking the food, there was no symptom of gastrointestinal upset, diarrhea and etc. After taking granules of food No. 1, there was no abnormality in hepatorenal function indicators and no obvious change in hemogram; the symptom of fear of chill was relieved and even disappeared; body weight as well as appetite of the patient was improved, and mental state became better; colleagues or friends of the patient deemed that the patient was significantly improved. With medicine therapy coordinated positively, the patient's life quality was obviously improved.

Example 2. Application Effect of Soup of Food Obtained in Embodiment 1

There were 100 volunteers with AIDS, whose blood examination result was HIV positive (+). Before taking the food, all of them have one or more of the following symptoms: fever, shiver with cold, joint pain, muscle pain, vomit, diarrhea, laryngalgia with persistent fever, night sweat, enervation, systemic superficial lymphadenopathy, body weight loss over 10% in 3 months even 40% at most, becoming thin obviously, appetite decreasing, apocleisis, sicchasia, hematochezia, dizziness, headache, lags in response, hypophrenia, insanity, convulsions, hemiplegic paralysis, dementia, diffuse papules, acute posterior ganglionitis, inflammation and fester in oral cavity and pharyngeal mucosa. Taking said granules of food No. 1 for continuous 10 days, it's indicated in 97 volunteers that their symptoms of pains and fear of chill were relieved and even disappeared; complications were relieved obviously and even disappeared. And there was no new complication raised in any one, and their mental states became better. Furthermore, according to data distribution of life quality score before and after eating soup of food No. 1, the total effective rate reaches 97%. The data distribution of life quality score before and after eating soup of food No. 1 is shown in table 1.

Table 1 the data distribution of life quality score before and after eating said soup of food obtained in embodiment 1

| Number of AIDS patients | Time | life quality score (point) | | | | |
| --- | --- | --- | --- | --- | --- | --- |
| | | <20 | 21-30 | 31-40 | 41-50 | 51-60 |
| 100 | Before eating soup of food no. 1 | 4 | 44 | 40 | 10 | 2 |
| | After eating soup of food no. 1 | 0 | 3 | 36 | 49 | 12 |

Typical Case:

Name: XXX; sex: X; born in XX; address: XX; profession:

Blood examination result: HIV positive (+)

Symptoms: apocleisis, skin being easy to be damaged with haemophilia, fatigue and lack of strength, diarrhoea, dizziness, headache, lags in response, hypophrenia, insanity, systemic pruritus. XXX took soup of food No. 1. During the period of taking, there was no symptom of gastrointestinal upset, diarrhea and etc. After taking soup of food No. 1, there was no abnormality in hepatorenal function indicators and no obvious change in hemogram; the symptom of fear of chill was relieved and even disappeared; body weight as well as appetite of the patient increased, and mental state became better; colleagues and friends of the patient admitted the patient was significantly improved. With medicine therapy coordinated positively, the patient's life quality was obviously improved.

Example 3. Application Effect of Powder Obtained in Embodiment. 1

There were 100 volunteers with AIDS, whose blood examination result was HIV positive (+). Before taking the food, their all have one or more following symptoms: fever, shiver with cold, joint pain, muscle pain, vomit, diarrhea, laryngalgia with persistent fever, night sweat, enervation, systemic superficial lymphadenopathy, body weight loss over 10% in 3 months even 40% at most, becoming thin obviously, appetite decreasing, apocleisis, sicchasia, hematochezia, dizziness, headache, lags in response, hypophrenia, insanity, convulsions, hemiplegic paralysis, dementia, diffuse papules, acute posterior ganglionitis, inflammation and fester in oral cavity and pharyngeal mucosa. Taking said powder of food No. 1 once every day for continuous 10 days, its indicated in 97 volunteers that their symptoms of pains and fear of chill were relieved and even disappeared; complications were relieved obviously and even disappeared. And there was no new complication raised in any one, and their mental states became better. Furthermore, according to data distribution of life quality score before and after eating powder of food No. 1, the total effective rate reaches 97%. The data distribution of life quality score before and after eating powder of food No. 1 is shown in table 1.

Table 1 the data distribution of life quality score before and after eating said powder of food obtained in embodiment. 1

| Number of AIDS patients | Time | life quality score (point) | | | | |
| --- | --- | --- | --- | --- | --- | --- |
| | | <20 | 21-30 | 31-40 | 41-50 | 51-60 |
| 100 | Before eating powder of food no. 1 | 4 | 44 | 40 | 10 | 2 |
| | After eating powder of food no. 1 | 0 | 3 | 36 | 48 | 12 |

Typical Case:

Name: XXX; sex: X; born in XX; address: XX; profession:

Blood examination result: HIV positive (+)

Symptoms: persistent fever, apocleisis, fatigue and lack of strength, enervation, night sweat, diarrhoea, dizziness, headache, lags in response, hypophrenia, insanity, systemic pruritus. XXX took powder of food no. 1. During the period of taking, there was no symptom of gastrointestinal upset, diarrhea and etc. After taking soup of food No. 1, there was no abnormality in hepatorenal function indicators and no obvious change in hemogram; the symptom of fear of chill was relieved and even disappeared; body weight as well as appetite of the patient increased, and mental state became better; colleagues and friends of the patient admitted that the patient was significantly improved. With medicine therapy coordinated positively, the patient's life quality was obviously improved.

Example 4. Application Effect of Granules Obtained in Embodiment 2

There were 60 volunteers with AIDS, whose blood examination result was HIV positive (+). Before this test their all have one or more of following symptoms: fever, shiver with cold, joint pain, muscle pain, vomit, diarrhea, laryngalgia with persistent fever, night sweat, enervation, systemic superficial lymphadenopathy, body weight loss over 10% in 3 months even 40% at most, becoming thin obviously, appetite decreasing, apocleisis, sicchasia, hematochezia, dizziness, headache, lags in response, hypophrenia, insanity, convulsions, hemiplegic paralysis, dementia, diffuse papules, acute posterior ganglionitis, inflammation and fester in oral cavity and pharyngeal mucosa. Taking said granules of food No. 2 once every day for continuous 10 days, it's indicated in 58 volunteers that their symptoms of pains and fear of chill were relieved and even disappeared; other complications were relieved obviously and even disappeared. And there was no new complication raised in any one, and their mental states became better. Furthermore, according to the data distribution of life quality score before and after taking granules of food No. 2, the total effective rate reaches 96.67%. The data distribution of life quality score before and after eating granules of food No. 2 is shown in table 2.

Table 2 the data distribution of life quality score before and after eating said granules of food obtained in embodiment 2

| Number of AIDS patients | Time | life quality score (point) | | | | |
|---|---|---|---|---|---|---|
| | | <20 | 21-30 | 31-40 | 41-50 | 51-60 |
| 60 | Before eating granules of food no. 2 | 2 | 22 | 20 | 14 | 2 |
| | After eating granules of food no. 2 | 0 | 2 | 13 | 37 | 8 |

Typical Case:
XXX sex: X born in XX address: XX profession:
Blood examination result: HIV positive (+)
Symptoms: skin being easy to be damaged with haemophilia, persistent fever, enervation, night sweat, appetite decreasing, flusteredness, dizziness, fatigue and lack of strength, drowsiness, lags in response, hypophrenia. XXX took granules of food No. 2. During the period of taking, there was no symptom of gastrointestinal upset, diarrhea and etc. After taking granules of food No. 2, the symptom of fear of chill disappeared gradually; body strength was recovered in fine feather; there was no new complication raised; body weight and immunity was enhanced, and the patient could accept AIDS medicine therapy actively.

Example 5. Application Effect of Soup Obtained in Embodiment 2

There were 60 volunteers with AIDS, whose blood examination result was HIV positive (+). Before this test their all have one or more of following symptoms: fever, shiver with cold, joint pain, muscle pain, vomit, diarrhea, laryngalgia with persistent fever, night sweat, enervation, systemic superficial lymphadenopathy, body weight loss over 10% in 3 months even 40% at most, becoming thin obviously, appetite decreasing, apocleisis, sicchasia, hematochezia, dizziness, headache, lags in response, hypophrenia, insanity, convulsions, hemiplegic paralysis, dementia, diffuse papules, acute posterior ganglionitis, inflammation and fester in oral cavity and pharyngeal mucosa. Taking said soup of food No. 2 once every day for continuous 10 days, it's indicated in 58 volunteers that their symptoms of pains and fear of chill were relieved and even disappeared; other complications were relieved obviously and even disappeared. And there was no new complication raised in any one, and their mental states became better. Furthermore, according to the data distribution of life quality score before and after taking soup of food No. 2, the total effective rate reaches 96.67%. The data distribution of life quality score before and after eating soup of food No. 2 is shown in table 2.

Table 2 the data distribution of life quality score before and after eating said soup of food obtained in embodiment 2

| Number of AIDS patients | Time | life quality score (point) | | | | |
|---|---|---|---|---|---|---|
| | | <20 | 21-30 | 31-40 | 41-50 | 51-60 |
| 60 | Before eating soup of food no. 2 | 2 | 22 | 20 | 14 | 2 |
| | After eating soup of food no. 2 | 0 | 1 | 13 | 38 | 8 |

Typical Case:
XXX sex: X born in XX address: XX profession:
Blood examination result: HIV positive (+)
Symptoms: diarrhea, persistent fever, enervation, night sweat, skin being easy to be damaged with haemophilia, appetite decreasing, flusteredness, dizziness, fatigue and lack of strength, drowsiness, lags in response, hypophrenia. XXX took soup of food No. 2. During the period of taking, there was no symptom of gastrointestinal upset, diarrhea and etc. After taking soup of food No. 2, the symptom of fear of chill disappeared gradually; there was no new complication raised; as to the patients, their physical strength was recovered; body weight increased; immunity was enhanced, and they were mettlesome so that they could accept AIDS medicine therapy actively.

Example 6. Application Effect of Powder Obtained in Embodiment 2

There were 80 volunteers with AIDS, whose blood examination result was HIV positive (+). Before this test their all have one or more of following symptoms: fever, shiver with cold, joint pain, muscle pain, vomit, diarrhea, laryngalgia with persistent fever, night sweat, enervation, systemic superficial lymphadenopathy, body weight loss over 10% in 3 months even 40% at most, becoming thin obviously, appetite decreasing, apocleisis, sicchasia, hematochezia, dizziness, headache, lags in response, hypophrenia, insanity, convulsions, hemiplegic paralysis, dementia, diffuse papules, acute posterior ganglionitis, inflammation and fester in oral cavity and pharyngeal mucosa. Taking said powder of food No. 2 once every day for continuous 10 days, it's indicated in 77 volunteers that their symptoms of pains and fear of chill were relieved and even disappeared; other complications were relieved obviously and even disappeared. And there was no new complication raised in any one, and their mental states became better. Furthermore, according to the data distribution of life quality score before and after taking powder of food No. 2, the total effective rate reaches 96.25%. The data distribution of life quality score before and after eating powder of food No. 2 is shown in table 2.

Table 2 the data distribution of life quality score before and after eating said powder of food No. 2

| Number of AIDS patients | Time | life quality score (point) | | | | |
|---|---|---|---|---|---|---|
| | | <20 | 21-30 | 31-40 | 41-50 | 51-60 |
| 60 | Before eating powder of food no. 2 | 6 | 26 | 24 | 18 | 6 |
| | After eating powder of food no. 2 | 0 | 3 | 18 | 44 | 15 |

Typical Case:
XXX sex: X born in XX address: XX profession:
Blood examination result: HIV positive (+)
Symptoms: dizziness, systemic pruritus, skin being easy to be damaged with haemophilia, persistent fever, enervation, night sweat, appetite decreasing, insanity, flusteredness, headache, fatigue and lack of strength, drowsiness, lags in response, hypophrenia. During taking the powder of food obtained in embodiment 1, there was no symptom of gastrointestinal upset, diarrhea and etc. After taking of the powder the symptom of fear of chill disappeared gradually; their physical strength was recovered; body weight as well as immunity of the patient increased and they could accept AIDS medicine therapy actively.

In this invention, 60 AIDS patients were invited as volunteers to eat the food containing 2.04~6.12 g granules, soup or powder of food no. 1 and food no. 2 respectively continually 10 days, and the symptom of fear of chill in more than 96% of the patients was relieved gradually or even disappeared; other symptoms were relieved correspondingly. The patients' life quality was improved significantly.

In addition, the inventor invited 120 volunteers who have just been found to carry HIV (HIV positive) to take the food of the invention. Said 120 volunteers were divided into 12 groups with 10 persons in each group, and they took 2.04~6.12 g granules, soup or powder of food No. 1 and food No. 2; or food containing 2.04~6.12 g granules, soup or powder of food No. 1 and food No. 2 respectively for half a year. They were conducted with HIV test and complications test when the research period of half a year ended, and the results showed complications set in later in all volunteers' body than ordinary AIDS patients. The food has 100% effective rate in slow down disease course of AIDS. It's demonstrated by this results that, eating said granules, soup or powder of this invention in long term or eating food containing said granules, soup or powder of this invention in long term can prevent AIDS effectively.

It's indicated through the above examples, with regard to AIDS patients who eat said food for nutritional therapy of AIDS provided in this invention, their systemic nutritional states are improved; erythrocyte decay is inhibited obviously; the symptom of fear of chill was relieved and cured; their body weights are no longer decreased basically; opportunistic infection was controlled. Eating said food of this invention can establish base for further medicine therapy and strengthen the confidence of AIDS patients whose life quality is improved significantly.

The invention claimed is:

1. A nutritional supplement for nutritional therapy of AIDS, comprising:
    a liquid medium including a water-leach liquor of a crude drug of *Callicarpa bodinieri;*
    deeply fermented maternal strains hypha of *Morchella* spp within the liquid medium; and
    deeply fermented maternal strains hypha of *Tricholoma matsutake* within the liquid medium.

2. The nutritional supplement of claim 1, wherein the weight ratio between the crude drug used for preparing said water-leach liquor and prepared said water-leach liquor (crude drug:water leach liquor) is 4~5:100.

3. The nutritional supplement of claim 2, further comprising an adjuvant, wherein the components of the adjuvant by part of weight are approximately:
    1 part of pulse flour,
    1 part of corn flour,
    2 parts of white sugar,
    0.1 parts of dipotassium hydrogen phosphate,
    0.1 parts of potassium dihydrogen phosphate, and
    0.05 parts of magnesium sulfate.

4. The nutritional supplement of claim 3, wherein form of the nutritional supplement is granules, soup or powder.

5. The nutritional supplement of claim 3, wherein said water-leach liquor is extracted from the root of *Callicarpa bodinieri.*

6. The nutritional supplement of claim 5, wherein form of the nutritional supplement is granules, soup or powder.

7. The nutritional supplement of claim 1, wherein form of the nutritional supplement is granules, soup or powder.

8. A method of preparing a nutritional supplement for nutritional therapy of comprising:
    (1) preparing a water-leach liquor of the crude drug of *Callicarpa bodinieri;*
    (2) diluting the water-leach liquor by adding 20~25 times of water in volume to obtain a traditional Chinese medicine liquid medium;
    (3) adding maternal strains of *Morchella* spp and *Tricholoma matsutake* in said traditional Chinese medicine liquid medium and conducting deep fermentation.

9. The method of claim 8, wherein said deep fermentation comprises:
    inactivating by water vapour under ordinary pressure;
    cooling to 26±2° C.; and
    fermenting for 60~144 hours.

10. The method of claim 8, wherein, in step (1), the weight ratio between the crude drug used for preparing said water-leach liquor and prepared said water-leach liquor (crude drug:water leach liquor) is 4~5:100.

11. The method of claim 10, wherein said deep fermentation comprises:
    inactivating by water vapour under ordinary pressure;
    cooling to 26±2° C.; and
    fermenting for 60~144 hours.

12. The method of claim 10, further comprising, as part of step (2):
    adding an adjuvant into the water-leach liquor, wherein the added adjuvant has 4~5 times of weight of the crude drug; and
    conducting elixation of the water-leach liquor, wherein:
        the constituents of the adjuvant by part of weight are approximately:
            1 part of pulse flour,
            1 part of corn flour,
            2 parts of white sugar,
            0.1 parts of dipotassium hydrogen phosphate,
            0.1 parts of potassium dihydrogen phosphate, and
            0.05 parts of magnesium sulfate.

13. The method of claim 12, wherein said deep fermentation comprises:
    inactivating by water vapour under ordinary pressure;
    cooling to 26±2° C.; and
    fermenting for 60~144 hours.

* * * * *